(12) United States Patent
Joyce et al.

(10) Patent No.: US 9,188,550 B2
(45) Date of Patent: Nov. 17, 2015

(54) CROSS CALIBRATION OF TWO ENERGY DISPERSIVE X-RAY BAGGAGE SCREENING SYSTEMS INCLUDING TRANSFORMATION OF THE REFERENCE DATABASE

(75) Inventors: David Edward Joyce, Bearpark (GB); Timothy Simon Wright, Sedgefield (GB); Ian Radley, Bishop Auckland (GB)

(73) Assignee: Kromek Limited, Durham (GB)

( * ) Notice: Subject to any disclaimer, the term of this patent is extended or adjusted under 35 U.S.C. 154(b) by 727 days.

(21) Appl. No.: 13/521,810

(22) PCT Filed: Jan. 10, 2011

(86) PCT No.: PCT/GB2011/050021
§ 371 (c)(1),
(2), (4) Date: Sep. 18, 2012

(87) PCT Pub. No.: WO2011/086366
PCT Pub. Date: Jul. 21, 2011

(65) Prior Publication Data
US 2013/0013242 A1    Jan. 10, 2013

(30) Foreign Application Priority Data

Jan. 12, 2010   (GB) .................................. 1000446.3
Aug. 26, 2010   (GB) .................................. 1014220.6

(51) Int. Cl.
*G01N 23/02*    (2006.01)
*G01N 23/087*   (2006.01)

(52) U.S. Cl.
CPC .................................. *G01N 23/087* (2013.01)

(58) Field of Classification Search
CPC .............................. G01N 23/02; G06F 19/00
USPC ........................................................ 250/252.1
See application file for complete search history.

(56) References Cited

U.S. PATENT DOCUMENTS

| 4,864,842 | A | 9/1989 | Regimand |
| 5,768,334 | A | 6/1998 | Maitrejean et al. |

(Continued)

FOREIGN PATENT DOCUMENTS

| WO | WO 2008/142446 | 11/2008 |
| WO | WO 2009/024817 | 2/2009 |
| WO | WO 2009/024818 | 2/2009 |
| WO | WO 2010/086636 | 8/2010 |

OTHER PUBLICATIONS

A Benmalek et al.: "Comparision and Cross-Calibration of DXA Systems: ODX-240 and Sophos L-XRA versus Hologic QDR-4500, for Spinal Bone Mineral Measurement", *Osteoporosis International*, vol. 8, Jan. 1, 1998, pp. 570-577.

(Continued)

*Primary Examiner* — Marcus Taningco
(74) *Attorney, Agent, or Firm* — Drinker Biddle & Reath LLP (57) ABSTRACT

A method of calibration of a dataset for spectroscopically resolved radiation scanning, comprising the steps of: generating an apparatus condition specific calibration dataset of emergent radiation intensity information generated after interaction in the scanning zone of at least one standard object spectroscopically resolved into a plurality of frequency bands; providing a transferable database comprising a dataset of transferable data items of emergent intensity information for a range of component materials, each spectroscopically resolved into a plurality of frequency bands and linked to the condition specific calibration dataset; defining a reference calibration dataset; generating a transfer function between the data item and the reference calibration dataset; applying the transfer function to the transferable data item to generate a dynamic data item adjusted to the reference calibration; populating a data register with a dynamic dataset comprising a dataset of data items each dynamically adjusted to the reference calibration.

19 Claims, 4 Drawing Sheets

(56) References Cited

U.S. PATENT DOCUMENTS

| | | | |
|---|---|---|---|
| 7,283,226 B2* | 10/2007 | Hasan | 356/237.4 |
| 7,355,709 B1* | 4/2008 | Bevis et al. | 356/390 |
| 2002/0175292 A1* | 11/2002 | Whitehouse et al. | 250/394 |
| 2004/0076260 A1* | 4/2004 | Charles, Jr et al. | 378/124 |
| 2005/0010106 A1* | 1/2005 | Lang et al. | 600/425 |

OTHER PUBLICATIONS

Kalender et al.: "The European Spine Phantom—a tool for standardization and quality control in spinal bone mineral measurements by DXA and QCT.", *European Journal of Radiology*, vol. 20, No. 2, Jul. 1, 1995, pp. 83-92.

Sydney Lou Bonnick: "Bone Densitometry in Clinical Practice Application and Interpretation"; *Humana Press*, Nov. 13, 2009, pp. xvii, xviii, 107, 108, 122-125, 152-157.

Harry K. Genant et al.: "Universal standardization for dual X-ray absorptiometry: Patient and phantom cross-calibration results", *Journal of Bone and Mineral Research*, vol. 9, No. 10, Oct. 1, 1994, pp. 1503-1514.

Jan Dequeker: "Quantitative Assessment of Osteoporosis", In: J.E.W. Beneken and V. Thevenin (Editors): "Advances in Biomedical Engineering", *IOS Press* 1993, pp. 133-151.

International Search Report, dated Aug. 2011.
International Written Opinion, dated Aug. 2011.

\* cited by examiner

CROSS CALIBRATION OF TWO ENERGY DISPERSIVE X-RAY BAGGAGE SCREENING SYSTEMS INCLUDING TRANSFORMATION OF THE REFERENCE DATABASE

FIELD OF THE INVENTION

The invention relates to the scanning of objects to gain information about their identity and/or material content using a radiation source. The invention relates in particular to a method of calibration of a dataset produced by an apparatus for scanning an object and to an apparatus adapted for calibration by such a method. The invention relates in particular to the implementation of a scanner calibration protocol comprising the generation and/or use of a reference database of information characteristic of a plurality of target materials and the population of a scanner database with dynamically calibrated reference information derived from such a reference database.

The invention particularly relates to an apparatus and method making use of high energy radiation such as x-rays or gamma-rays to scan objects where it is desirable to gain information relating to the material composition of the internal contents. The invention is particularly suited to application in conjunction with the scanning of contained liquids to determine the identity or composition of the contained liquid but is not limited to liquid applications. The invention may be applied in conjunction with a method and apparatus that operates by or in conjunction with the generation of an image of the material, but is not limited to imaging applications.

BACKGROUND

It is desirable to scan the contents of objects such as, for example, baggage containers, liquid containers etc, at security and customs checkpoints to gain information about content, for example to obtain an indication that the contents of the object do not constitute a threat to security or a breach of customs regulations. It is also desirable to scan the contents of objects for other purposes such as quality control, content verification, degradation monitoring etc.

It is known that information useful in this regard may be obtained from an analysis of radiation received at a detector after interaction with the object. To ensure that the contents of an object are what they are claimed to be, it may be useful to scan the object and contents so that a high energy ionising radiation beam traverses a cross section of the object. It can be possible to obtain an indication of the materials composition and/or identity from a numerical analysis of the resultant transmitted radiation beam intensity data and a comparison of the results of that analysis with a reference dataset relating equivalent pre-stored data to a range of expected constituent materials of a known composition and/or of a known identity to which unique data can be attributed. Information regarding the composition and/or identity of an object under test and/or its contents may then be inferred from a match of test data to pre-stored data.

The interaction of high energy ionising radiation with an object is the subject of a number of physical mechanism including various modes of absorption, diffraction, elastic and inelastic scattering which have been characterised to a greater or lesser degree. Many of these mechanisms vary characteristically with material content in a manner which is dependent upon the radiation wavelength/frequency.

Instrumentation has been developed which is intended to examine objects non-invasively to identify content materials, in particular for example liquids, within sealed containers by referencing such characteristic energy selective information to a database of such data for known materials. According to techniques disclosed for example in our co-pending International Patent Application Nos. WO2009/024817, WO2009/024818, and WO 2008/142446 a container may be irradiated with a beam of radiation and the transmission or other characteristics of the container and its liquid contents measured using an energy selective detector such as cadmium telluride or germanium.

The transmission or other characteristics of various materials could be recorded and held in a database. The database could then be used for comparison with in situ scanning of objects to look for matched transmission characteristics and, therefore, target materials could be identified.

A problem arises in that precise transmission data may be influenced by the apparatus conditions when it is collected. All instruments will vary to some degree however high a tolerance is designed in principle. Errors in build, such as component offsets and misalignments, cannot be eliminated. Sources necessarily exhibit some variation. Detector performances and sensitivities can never be perfectly matched. Even an individual instrument can vary in performance over time, eg as operating conditions change, if it is moved etc. Although good practices and standard processes can reduce these variations between instruments and apparatus conditions, they cannot be entirely eliminated.

Reference data from a reference database generated on another instrument or otherwise in other apparatus conditions can only be used on a current instrument to tolerances that take due account of these variations between apparatus conditions. This may be inadequate for the levels of precision required to differentiate multiple materials with closely related characteristics. The alternative, to populate the current instrument with a bespoke generated reference database, would be time consuming and, therefore, unsuitable for many intended uses, such as in airport security where time is often of the essence.

There is a need for an improved a method of calibration of a dataset produced by an apparatus for scanning an object for non-invasively identifying the composition of its contents so as to make the data more readily available to other apparatus or in other apparatus conditions. In a particular preferred case there is a need for an improved method of populating such an apparatus with dynamically calibrated reference information derived from a over an operationally practical timescale. In a further preferred case there is a need for an improved method of populating a central reference database with data generated from multiple apparatus according to a common reference standard.

SUMMARY OF THE INVENTION

In accordance with the invention in a first aspect a method of calibration of a dataset produced by an apparatus for scanning an object by causing incident radiation to impinge upon the object in a scanning zone and collecting spectroscopically resolved emergent intensity information of radiation after interaction with the object, comprising the steps of: generating an apparatus condition specific calibration dataset of emergent radiation intensity information generated after interaction in the scanning zone of at least one standard object spectroscopically resolved into a plurality of frequency bands;

populating a transferable database comprising a dataset of transferable data items of emergent intensity information for a range of possible component materials, each data item comprising emergent radiation intensity information for the material spectroscopically resolved into a plurality of frequency bands, and each data item being linked to a calibration dataset of emergent radiation intensity information generated by the said at least one standard object specific to the apparatus condition used to generate the said data item spectroscopically resolved into a plurality of frequency bands;

optionally repeating the foregoing step for a range of apparatus conditions; defining a reference calibration dataset of emergent radiation intensity information generated after interaction in the scanning zone of at least one standard object spectroscopically resolved into a plurality of frequency bands for a reference apparatus condition;

for each transferable data item:
generating a transfer function from the functional relationship between the calibration dataset linked to the data item and the reference calibration dataset;

applying the transfer function to the transferable data item to generate a dynamic data item adjusted to the reference calibration;

thereby populating a data register with a dynamic dataset comprising a dataset of data items of emergent intensity information for a range of possible component materials each dynamically adjusted to the reference calibration.

Each dataset of emergent intensity information, whether for a known material, for a standard object, or for an object under test is spectroscopically resolved into a plurality of frequency bands. The apparatus to which the method is applied is therefore an apparatus for the scanning of an object in a scanning zone by causing suitable radiation from a radiation source to be incident on an object in the scanning zone and collecting at a radiation detector system spaced therefrom information about incident radiation following interaction with the object that is spectroscopically resolved into a plurality of frequency bands.

The invention is characterised distinctively by the way in which a specific apparatus to be used is made able to access and make use of a reference database of emergent intensity information generated elsewhere for a suitable large range of likely component materials. In a likely mode of operation of the invention, this transferable reference database might have been generated over a prolonged period of time to be populated by intensity-related information for a large range of materials, and in particular specific target or contraband materials, from the use of similar apparatus on other occasions. In particular, such a general reference database might have been generated over different apparatus conditions from those which apply to the specific apparatus to be used, and in the case of a large reference database over many different apparatus conditions.

It is desirable that such a general transferable reference database could be made available as a reference database for any machine prior to use. However, the minor differences in operational parameters between individual machines will, for the reasons discussed above, impose limits to the tolerance to which data in raw form can be transferred to and/or referenced by different apparatus conditions.

In accordance with the invention, an entirely relative calibration is performed to mitigate this problem. A machine which is to be used to generate data for the transferable database is first subjected to a calibration step in which emergent intensity data is generated for a plurality of frequency bands in relation to at least one standard object. It is envisaged that in the calibration step reference data is generated for a plurality of frequency bands in relation to at least two standard reference points so that a calibration can be fitted between them by generation of a suitable transfer function. This generates a calibration dataset specific to the apparatus conditions.

Data used to populate the transferrable database is linked to this apparatus specific calibration dataset. The transferrable database may be further populated for a range of apparatus or apparatus conditions, data again linked to the appropriate apparatus specific calibration dataset.

All such data is relatively calibrated to a reference calibration dataset by applying the transfer function to the transferable data item to generate a dynamic data item adjusted to the reference calibration so as to populate a data register with a dynamic dataset comprising a dataset of data items of emergent intensity information for a range of possible component materials each dynamically adjusted to the reference calibration.

There are two principal methods by which this dynamically adjusted dataset may be made available as a reference dataset to a given further apparatus and/or under new apparatus conditions. Both rely on the generation, for the apparatus to be used, of a further apparatus condition specific calibration dataset for that apparatus to be used. Thus, a transfer function may again be used to effect a relative calibration between previously collected data for other apparatus conditions and data collected by the apparatus to be used.

In one possible method, the dynamically adjusted dataset may be used to populate a reference data register adjusted to the apparatus conditions of the apparatus in use. In this instance, the reference calibration dataset is based on a calibration of the apparatus to be used. The step of defining a reference calibration dataset comprises generating an apparatus condition specific calibration dataset for the apparatus to be used in the manner above described.

The method comprises the particular steps of:
generating a transfer function from the functional relationship between the calibration dataset linked to the data item and the calibration dataset generated for the apparatus to be calibrated;

applying the transfer function to the transferable data item to generate a dynamic data item adjusted to the apparatus to be calibrated;

thereby populating a data register addressable by the apparatus to be calibrated with a dynamic dataset comprising a dataset of data items of emergent intensity information for a range of possible component materials each dynamically adjusted to the apparatus to be calibrated.

In another possible method, the dynamically adjusted dataset is calibrated with respect to a reference standard, however defined, and data generated by the apparatus to be used is adjusted to the reference calibration as it is collected.

The method comprises the additional steps, for each measured data item on the apparatus to be used, of
generating a transfer function from the functional relationship between the calibration dataset linked to the apparatus to be used and the reference calibration dataset;

applying the transfer function to the measured data item to generate a data item adjusted to the reference calibration.

On some occasions it may be desirable to provide a machine with a machine-specific reference dataset in the manner of the first example method. A specific example of this application is described below. On other occasions it may be desirable to adjust machine-specific measurements to a standard reference. These and other examples of the use of a relative data calibration to relate measured data on a given apparatus to be used to reference data in a data register generated in and calibrated for other apparatus conditions can be envisaged. Where a specific example of the first application is given by way of illustration the skilled person will understand that the invention is not limited to such cases and will readily be able to apply aspects of the specific example to such other examples of the use of a relative data calibration.

A suitable calibration step for example provides for calibration measurement at a plurality of material thickness and/or for a plurality of material compositions etc. This might be achieved in that plural standard objects are provided and/or in that a standard object defines plural standard reference points, for example defining plural portions of different known thickness, composition etc.

It is envisaged that an identical or at least compatible standard object or set of standard objects should be used on other apparatus which has been used to populate the transferable database. There is thus a common calibration standard. Each data item of emergent intensity information for a particular material which has been introduced into the transfer database is specifically tied to calibration data based on this calibration standard.

The performance of given standard object and a given standard calibration process is susceptible to many fewer variables than the overall performance of different apparatus. In a preferred case, the calibration routine may additionally be modified to correct further for tool response over a range of varied conditions, for example intensity, material density etc. Accordingly, the use of a common calibration standard allows a relative transfer function to be generated to relate apparatus-specific data to different apparatus conditions with a suitable transfer adjustment between different apparatus conditions to a much higher degree of tolerance. This is underlying principle of the invention.

A transfer function is generated by numerical comparison of the standard results for the reference calibration dataset with data and the standard results for the apparatus used to generate each data item. Points of reference on the standard calibration data for the reference calibration dataset and the standard calibration data for the apparatus used to generate a given data item may be fitted together to generate a transfer function by interpolation to any suitable fitting routine, including for example linear, logarithmic, or other.

In a possible case, as discussed above, the method is used to populate a specific apparatus with reference data prior to use, and the reference calibration dataset is based on a calibration of the apparatus to be populated.

Each data item is then adjusted for the calibration of the apparatus to be populated with data accordingly. In this way, an apparatus to be used may be populated with a dynamic reference database derived from standard reference data from a range of sources which is specifically calibrated to the performance of the apparatus to be populated, but which has been generated previously, for example on other similar apparatus. Calibration of the apparatus prior to use comprises a relatively simple standard step. It is not necessary to populate the new apparatus by generation of apparatus specific emergent intensity data for the entire range of likely component materials. Instead, an entirely relative transfer methodology is used to transfer data from the transferable database into a form where it is specifically adjusted to the apparatus on which the dynamic database is to be populated.

Alternatively, the method is used to populate a central reference database with data generated from multiple apparatus according to a common reference standard.

Reference herein to intensity data, and to an intensity data item, should be understood to refer to any numerical data which can be related to the intensity of emergent radiation after interaction with an object. This should not be considered as limited to any strict measure of absolute intensity. Useful intensity data items might also comprise for example a relative measurement of emergent over incident intensity in which absolute intensity at the detector has been functionally related to initial intensity from the source, or to a data item which has been further numerically processed, for example to generate a material characteristic or parameter which is functionally dependent upon such an intensity relationship. In accordance with the principles of the invention, intensity information is collected and resolved into a plurality of frequency bands across the spectrum of the source. It further follows that it should understood that an intensity data item may be a data item at a single such band, or may represent a data item functionally related to intensity resolved in combined manner across a plurality of such bands. Thus, although for convenience and simplicity of language reference is generally made herein to "intensity data", this term will be understood to relate any data which is functionally related to and reflects the emergent intensity for a particular object, standard or material.

Reference made herein to emergent intensity is to the intensity received at a suitably placed detection apparatus after interaction of the incident radiation from the source with an object in the scanning zone. Any interaction where a known physical relationship can be used to relate emergent intensity to incident intensity in suitable functional manner which varies spectroscopically across the plurality of frequency bands into which the emergent data is resolved can be used for the purposes of the invention. The invention finds particularly useful application in relation to the scanning of objects to measure attenuation of transmitted radiation intensity, in particular by photoelectric absorption effects, and examples of the application of the invention are discussed with reference to such apparatus, but the invention should not be considered limited to such apparatus.

The invention finds particularly useful application in relation to the scanning of objects comprising containers of contained materials which by their nature will be expected to have a single generally homogeneous composition, for example fluid compositions such as liquids, including mixtures, solutions, emulsions, suspensions etc, like flowable compositions such as gels, pastes, creams, fine powders, and the like, aerosols etc. References by example to contained liquids in objects such as liquid containers should be understood as applicable to all such liquid, partly-liquid and other flowable materials having this essential mixed and generally homogeneous character when contained.

However, it should be understood that the invention is not limited to such liquids applications, and many of general principles of the invention may be equally applicable to heterogenous objects with solid and/or liquid contents. Example implementations of the invention with reference to liquids will be understood accordingly.

In accordance with the invention in a second more complete aspect a method of generation of a transferable reference database for an apparatus for scanning an object by causing incident radiation to impinge upon the object in a scanning zone and collecting spectroscopically resolved emergent intensity information of radiation after interaction with the object, and of populating a specific apparatus with a dynamic reference database derived therefrom, comprises the steps of:

generating an apparatus specific calibration dataset of emergent radiation intensity information generated after interaction in the scanning zone of at least one standard object spectroscopically resolved into a plurality of frequency bands;

generating a material specific transferable data item comprising emergent radiation intensity information generated after interaction in the scanning zone of an object of known material composition and/or identity spectroscopically resolved into a plurality of frequency bands;

linking the material specific transferable data item to the apparatus specific calibration dataset;

repeating the preceding two steps for a plurality of objects of known material composition and/or identity to populate a transferable database comprising a dataset of transferable data items of emergent intensity information for a range of possible component materials;

optionally repeating all the foregoing steps for further apparatus to further populate the transferable database;

applying the transferable database to the method of the first aspect of the invention.

Thus, the second aspect of the invention comprises in a first stage a method of populating a transferable database for use in accordance with the first aspect of the invention, and in a second stage making use of that transferable database in accordance with a first aspect of the invention.

Although reference is made herein to a "material specific transferable data item" for a data item obtained from an object of known material composition and/or identity, it is important to emphasise that this does not require that the material composition per se is known. The object or material needs to produce a defined response that potentially identifies it in unique manner by comparison with a database of equivalent responses. Such a response is materials dependent, and to that extent the data is material specific. However both the calibration and the comparison steps are potentially entirely relative, with no requirement to generate per se compositional data at any point.

In accordance with the foregoing method, a transferable database may be populated by generating emergent intensity data for a plurality of objects of known material composition and/or identity, homogenous or heterogeneous, and in particular for a range of target materials or objects which it is desired to identify. For each such source machine, data may be obtained for a large plurality of objects of likely composition. The database from each source machine in a preferred case comprises a component database of a larger global transferable database.

The procedure is for example as follows.

Before data is derived for a first set of machine conditions a calibration procedure is followed to generate a calibration dataset for those machine conditions. A calibration dataset comprises calibration data items for a plurality of scanning conditions at a plurality of energy bins. A component database of transferable intensity-related information for a range of objects/materials is then generated, to comprise a population dataset. For each component making up the population dataset a scan is performed of the relevant scan item, and emergent intensity data is resolved into plurality of energy bins. This population dataset is tied in cross-referenced manner to the applicable calibration dataset. The process may be repeated for second and subsequent machine conditions to generate further population datasets tied to further applicable calibration datasets and merged into the global transferable database.

A similar calibration procedure is followed to generate a calibration dataset for a machine to be populated. A suitable transfer function is applied to convert each data item in the transferable database so that it more accurately reflects an expected data item which would be expected to be generated by an identical object/material on the machine to be populated.

The power of such a database population and transfer protocol is apparent. Without a suitable transferable database which could be transferred in a useable and meaningful manner between the machines operating in different machine conditions it would be necessary to populate any reference database independently for a given machine condition. Such a process could be prohibitively time consuming and expensive for a realistic range of materials. Data could not be transferred between apparatus with certainty. Even for a given apparatus, a recalibration would require a further repopulation.

By contrast, the protocol of this aspect of the invention allows a global transferable database to be built up over time from a plurality of apparatus with potentially differing operational parameters operating at potentially differing conditions, but in such a manner that the transferable database can readily be transferred to form a dynamic reference database suitably calibrated against any operational apparatus.

A transferable database may be built up by generation of population data items during specific operation of a machine for that purpose, or may be populated by generation of population data items during operation of the machine for its primary intended purpose. By the same token it follows that material specific data items generated by the specifically calibrated apparatus may be fed back into a global transferable database.

In accordance with this refinement of the invention, the method of the first aspect comprises the further steps of:

generating a material specific transferable data item comprising emergent radiation intensity information generated after interaction in to the scanner zone of an object of known material composition and/or identity spectroscopically resolved into a plurality of frequency bands;

linking the material specific transferable data item to the apparatus specific calibration dataset generated previously;

passing the foregoing information to the transferable database to further populate the transferable database.

In a further refinement of the invention, the apparatus to be provided with a dynamic database in accordance with the first aspect of the invention need not be a physical apparatus having physical existence. Such apparatus may instead be a virtual apparatus created for theoretical testing and/or design optimisation purposes. Thus, in accordance with this possible refinement a method in accordance with the second aspect of the invention is used to provide a dynamic database for a virtual apparatus, for example for a Monte Carlo simulation.

The calibration process in accordance with the invention uses at least one standard object. Such at least one standard object is used to calibrate the apparatus to be calibrated in accordance with the first aspect of the invention, and an equivalent at least one standard object is used in the population of the transferable database. The said standard object(s) must be at least equivalently compatible so as to allow for co-operative numerical processing of the calibration datasets to generate the necessary transfer functions. Most conveniently, a standard object is identically conformed and standard measurement protocols are identically employed to maintain this compatibility. Alternatively, at least a known functional relationship must be maintained between different standard objects and/or protocols so as to enable numerical calculation of a suitable transfer function in accordance with the foregoing.

A suitable calibration standard provides reference data for at least two calibration points, for example at different material thickness and/or compositions etc. A suitable standard object preferably provides for calibration measurement at a plurality of material thickness and/or for a plurality of material compositions. Additionally or alternatively, a plurality of standard objects may be used.

A particularly convenient standard object comprises a standard block of known material with a plurality of discrete thickness. For example, a standard block is a block wedge. However, any standard object which gives good reproducibility can be employed.

Having regard to the possibility of application of the invention to a virtual apparatus, a virtual standard object may also be employed.

In the preferred case, a first standard object is used to calibrate a first system which generates data for a transferable database. An essentially identical standard object is used to obtain a calibration dataset on the system to be calibrated and populated with a dynamic database. The calibration dataset is resolved into a plurality of energy bins, and for example in the example case for a plurality of wedge thicknesses. A set of transfer functions (one for each energy bin) may be calculated by fitting the calibration datasets for the two machines. It thus follows that transmission data for any scanned item in the database can be transferred from a first system to a second system by applying the transfer function in a relative manner without requiring specific absolute calibration of either system.

Such a standard object can be manufactured to high tolerances, and will thus enable a relative transition between systems which inherently takes account of the variation between those systems without needing to evaluate those differences specifically.

In a possible embodiment intensity information collected for an object under test during a scanning step is numerically analysed against a suitable functional relationship relating emergent to incident intensity and the results compared with a library of suitable data with the objective of providing an indication of material content. For example, a ratio is determined of incident and transmitted intensity, and this ratio is used to determine a coefficient of mass attenuation, which can then be related to a library of equivalent coefficient data for expected target or component materials to gain information about the likely composition of the object and contents under scan. However, it is an advantage of the method that since a reference database is populated for typical material signatures, such a numerical analysis may be unnecessary, and identification may instead be made by a mere comparison of the measured emergent intensity data with such a database.

The object being scanned can be positioned stationarily in the scanning zone or for movement in the vertical or horizontal plane or any other direction depending on the application. For security or customs screening of liquids in bottles it is envisaged that the bottle may be mounted in a holder and moved through a generally vertical plane as mounting the bottle horizontally could result in spillage of threat materials. Mounting an object such as a bottle for vertical movement would require some sort of fastening to keep the object in place during the scanning movement so the object is preferably mounted at an angle of between 1° and 80° from vertical, preferably at an angle of between 5° and 45° and more preferably between 5° and 30°.

Many objects, such as containers, and for example bottles or cartons of liquids, have a regular shape defining a through thickness direction through which they might usually be scanned. For example such a thickness might be defined by the parallel sides of an object, or by diametrically opposite points on the surface of an object. The radiation beam can be arranged so that it is incident perpendicular to the surface of such an object. That is to say, it passes through an object normally to its surface and in such a through thickness direction. If the radiation beam is arranged to pass through the object at an angle other than perpendicular then the beam passes through an increased thickness of the object contents which can improve beam absorption and hence analysis of the object contents. For example, the radiation beam is preferably arranged to pass through an object at an angle of between 1° and 80° away from normal to the surface, preferably between 5° and 45° and more preferably between 5° and 30°. If the object is mounted at an angle of between 1° and 80°, preferably between 5° and 45° and more preferably between 5° and 30° such as is described above, then using a generally horizontal beam arrangement will give the desired increase in beam path length through the object contents.

The radiation source preferably comprises a source to deliver high-energy radiation such as ionising radiation, for example high-energy electromagnetic radiation such as x-rays and/or gamma rays, and the detection system is adapted correspondingly to detect radiation in this spectrum. The radiation source for example is a broadband source such as a broadband x-ray or gamma-ray source capable of producing broad spectrum emission over a wide range of energies.

In accordance with the general principles of the invention radiation is resolved spectroscopically across a plurality of energy bands within the source spectrum. Intensity related information is resolved into a plurality of differentiated energy bands in the sense that it is differentiated simultaneously into plural separate energy bands across the spectrum of the source. In the preferred case, incident radiation is resolved spectroscopically across at least three and more preferably at least five energy bands within the source spectrum. This can produce data susceptible of more powerful manipulation than monochromatic data.

So long as the spectrum is resolved into a plurality of energy bins, the bandwidth is not directly pertinent to the invention and useful results can be obtained by any suitable approach to dividing the spectrum, either in whole or in part, into separate bands. For example, the entire spectrum or a substantial part thereof may simply be divided between such a plurality of bandwidths, and each data item be considered as a measure representative of intensity across the entire band, and for example an average intensity. Alternatively, a plurality of relatively wide bands, but with discrete gaps therebetween, may be envisaged and analysed on the same basis. Alternatively, "bands" may be narrow even to the point where they essentially approximate to an evaluation of intensity at a single energy. As used herein the concept of intensity at an energy "band" includes evaluation of intensity at such a discrete single energy as well as evaluation of intensity at an energy across a narrow or broad bandwidth. The detector system is adapted to generate spectroscopic information about emergent radiation incident upon it at least to the extent of resolving a plurality of energy bands across the spectrum of the source, preferably at least three and preferably at least five energy bands, in the sense that it is adapted to differentiate incident radiation simultaneously into plural separate energy bands across the spectrum of the source. The detector system preferably exhibits a spectroscopically variable response across at least a part of the source spectrum allowing such simultaneous differentiation of incident radiation into plural energy bands and thus allowing spectroscopic information to be retrieved and intensity information to be detected at a plurality of differentiated energy bands across the spectrum of the source. Preferably the detector exhibits a spectroscopically variable response across at least a substantial part of the spectrum of the radiation source allowing detailed spectroscopic information to be retrieved.

The source may be a single broad spectrum source across which a plurality of bandwidths or single energies may be identified. Alternatively or additionally sources may be provided having narrow bandwidths or generating incident radiation at one or more discrete energies to provide some of the energies for comparison in accordance with the method of the invention. In this case the radiation source is a plural source comprising a combination of sources at different energies to provide the necessary total spectrum spread to allow resolution by the detector across a plurality of energies/energy bands.

For example a plural source comprises an x-ray source having a relatively lower energy spectrum, for example operating below 60 keV and for example at 10 to 50 keV and one or more radioisotope sources generating radiation at higher energies, for example above 100 keV.

The source is preferably capable of generating a sufficiently broad spectrum of radiation to enable the spectral resolution necessary for the performance of the invention. Preferably the source generates radiation across at least one or more parts of the range of 20 keV to 1 MeV, and more preferably across at least a part, and for example a major part, of the range of 20 keV to 160 keV. For example the source generates radiation ranging across at least one bandwidth of at least 20 keV within the given range. For example the spectrum is such that at least three 10 keV bands can be resolved within that range.

It is preferable that the detector system is enabled to detect radiation in a manner which is spectroscopically resolvable by the data processing apparatus. Preferably, a detector system, or some or all discrete detector elements making up a multi-element system, may be adapted to produce spectroscopic resolution in that it exhibits a direct spectroscopic response. In particular a system or element is fabricated from a material selected to exhibit inherently as a direct material property a direct variable electrical and for example photoelectric response to different parts of the source spectrum. For example, the detector system or element comprises a semiconductor material or materials preferably formed as a bulk crystal, and for example as a bulk single crystal (where bulk crystal in this context indicates a thickness of at least 500 µm, and preferably of at least 1 mm). The materials making up the semiconductor are preferably selected from cadmium telluride, cadmium zinc telluride (CZT), cadmium manganese telluride (CMT), germanium, lanthanum bromide, thorium bromide. Group II-VI semiconductors, and especially those listed, are particularly preferred in this regard. The materials making up the semiconductor are preferably selected from cadmium telluride, cadmium zinc telluride (CZT), cadmium manganese telluride (CMT) and alloys thereof, and for example comprise crystalline $Cd_{1-(a+b)}Mn_aZn_bTe$ where $a+b<1$ and a and/or b may be zero.

Combination of these and any other such materials may be considered which give spectroscopic detection rather than merely detecting amplitude of radiation after interaction with object and contents.

In a further complete aspect of the invention, a method of identifying the composition and/or identity of an object is provided which comprises calibrating a scanner apparatus and populating a scanner apparatus with a dynamic reference database in accordance with the first aspect of the invention;

causing an object of unknown composition and/or identity to be placed into a scanner zone between a radiation source and a radiation detector system spaced therefrom;

obtaining a dataset of emergent radiation produced by the object in the scanner zone after interaction with incident radiation;

resolving the collected emergent intensity data spectroscopically across a plurality of frequency bands in the spectrum of the source;

comparing the resolved intensity data with intensity data items in the dynamic reference database;

obtaining thereby an indication of the material content and/or identity of the object.

BRIEF DESCRIPTION OF THE DRAWINGS

The invention will now be described by way of example only with reference to the accompanying drawings in which.

DESCRIPTION OF THE PREFERRED EMBODIMENTS

Figure 1:
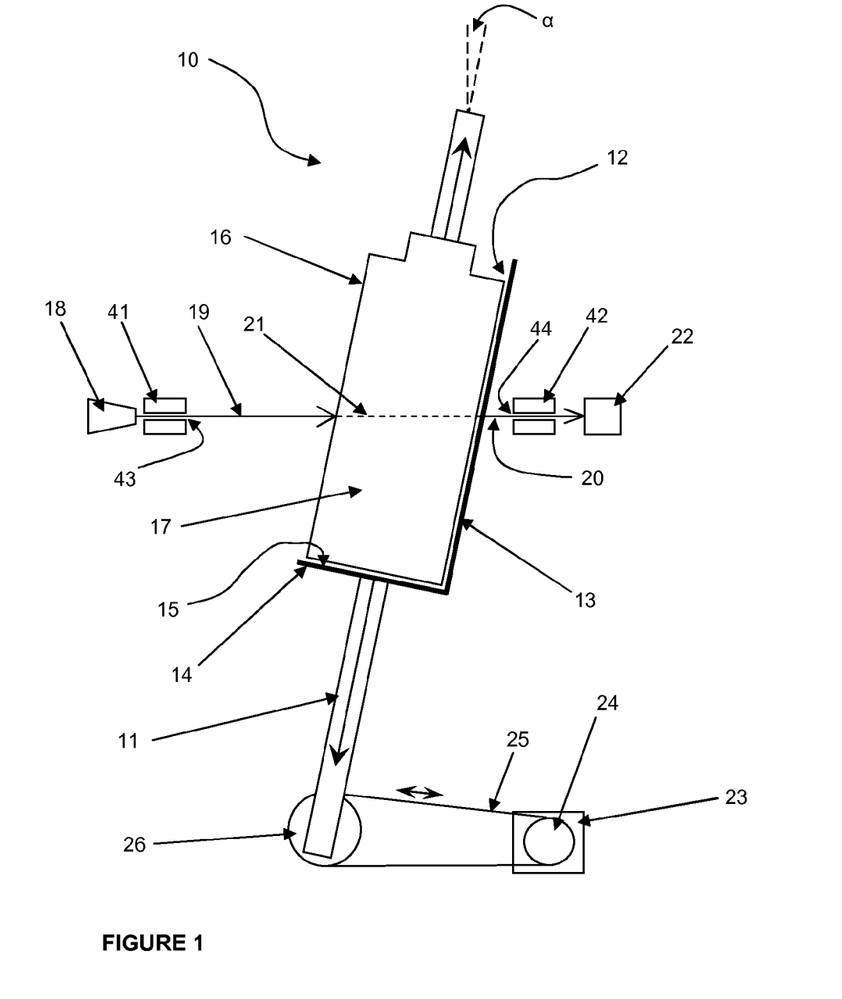
FIG. 1 is a schematic representation of a scanning apparatus to which the invention could relate, particularly adapted for the scanning of contained liquids.

In the apparatus illustrated in FIG. 1 an embodiment of a possible apparatus which might make use of the method of the invention or a dynamic database generated by the method of the invention is shown comprising a bottle scanner for scanning liquids in bottles and like objects using x-ray radiation.

In the illustrated embodiment, the principles of the invention are envisaged in use to provide a machine with a machine-specific reference dataset in the manner of one example of the method. On other occasions it may be desirable to adjust machine-specific measurements to a standard reference. These and other examples of the use of a relative data calibration to relate measured data on a given apparatus to be used to reference data in a data register generated in and calibrated for other apparatus conditions can be envisaged by the skilled person who will readily be able to apply aspects of the specific example below to such other examples of the use of a relative data calibration.

In the illustrated embodiment the bottle scanner 10 is provided with a linear slider shaft 11 to move a bottle holder 12 that is fixedly connected to the linear slider shaft 11 for movement therewith. The linear slider shaft 11 is capable of moving the bottle holder 12 in two directions.

The bottle holder 12 comprises a back member 13 against which the bottle 16 rests and a base member 14 with a top surface 15 onto which the bottle 16 sits. The bottle 16 is nested against and into the bottle holder 12 by virtue of the holder and linear slider shaft being inclined at an angle α. In the example this might be an angle of 15° from vertical. For a bottle, an angle of between 5° and 30° might be convenient. Other shapes of objects or containers might be held at different optimum angles.

The bottle holder back member 13 is preferably provided with an opening (not shown) to allow a clear path for the x-ray beam to pass from the bottle to the detector. The opening in the back member 13 could be a slot shaped aperture running from the top to the bottom of the back member. The slot aperture could be a narrow slot that provides some beam collimation with a width sufficient to allow the beam to pass through unimpeded but narrow enough to restrict any scatter radiation from reaching the detector 22. Additional or other alternative collimation of the beam on the transmission side could be provided.

The movement of the bottle holder 12 and bottle 16 along the linear slider shaft 11 is caused by the rotation of the electrically powered stepper motor 23. The motor causes the pulley 24 to rotate, which drives belt 25 which, in turn, drives the rotation of pulley 26. The rotational motion of pulley 26 is converted into a rotation of a suitable drive such as a screw drive (not shown) in the linear slider shaft 11 which creates the linear motion of the bottle holder 12.

The motor is capable of rotation in either direction and by controlling the direction of rotation of the motor the direction of movement of the bottle holder 12 and bottle 16 can be determined.

As the bottle is moved along the direction of the linear slider shaft it is caused to pass through an x-ray beam 19. The incident beam 19 is generated by a source 18, preferably a tungsten source so that it has a broad spectrum of energies present in the beam.

The x-ray beam 19 is aligned horizontally. As the bottle is inclined at an angle α from the vertical the beam does not strike the bottle perpendicular to the bottle's surface. This preferred arrangement gives an increased absorption path for the beam as it passes through the bottle and its contents.

The incident beam 19 passes through the bottle 16 and bottle contents 17 where absorption and scatter will take place along beam path 21 before the transmission beam 22 emerges from the bottle and is detected by detector 20.

The x-ray beam is preferably collimated by primary collimator 41 provided with aperture 43 and positioned close to the source 18 and is preferably a pencil beam with one dimensional geometry.

The transmission x-ray beam 20 is preferably collimated through an appropriate aperture 44 in secondary collimator 42 before it arrives at detector 22.

The detector 22 is preferably a single pixel aligned with the collimated x-ray beam. The detector generates a signal representative of the intensity and energy of interactions with photons from the transmission x-ray beam 20. These signals are then processed as detailed in FIG. 2 below. In the embodiment the detector comprises material capable of spectroscopic resolution of incident x-rays, and in the specific example comprises cadmium telluride (CdTe) although it will be appreciated that alternative materials could be used.

Additional analysis capability could be provided by the use of additional detectors to detect those parts of the x-ray beam that have been scattered in the forward and/or backwards directions. The transmission beam 20 and forward scattered x-ray beams could be detected by the use of linear or area arrays.

Figure 2:
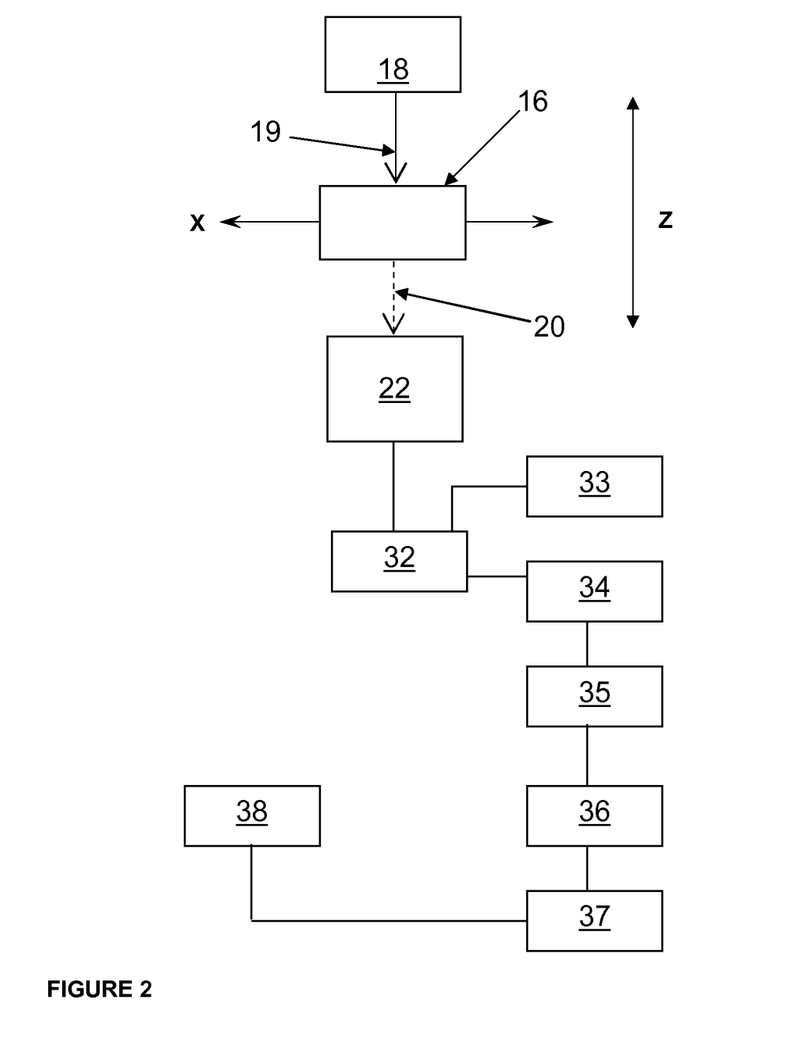
FIG. 2 is general schematic of a possible embodiment of more complete system to identify liquids from the scanning apparatus of FIG. 1.

In the general schematic representation of FIG. 2, a single ray path only is shown for simplicity. An x-ray source 18 and laterally spaced detector apparatus assembly 22 together define a scanning zone Z between them. In use, a bottle to be scanned is brought into an x-ray beam path by being placed in a bottle holder such as that shown in FIG. 1 and being moved in direction X through the scanning zone by a mechanism such as that described in FIG. 1 such that the x-ray beam passes through the bottle along its axis.

In the illustrated example, a bottle sits in the scanning zone Z. An incident beam 19 from the x-ray source is illustrated. In this simple schematic, the incident beam is represented by the line 19. The transmitted beam 20 is incident upon a single detector 22.

The detector 22 is in data communication with a processor 32. The inherent spectral resolution of the material in the detector allows the processor 32 to resolve the transmitted intensity data differentially across a plurality of pre-set frequency/energy bands in accordance with the principles of the invention by reference to energy band boundaries stored in the data register 33.

In the example embodiment a tungsten x-ray source, is used. A typical spectrum such as might be generated by tungsten of initial intensity against wavelength is illustrated in FIG. 3.

Figure 3:
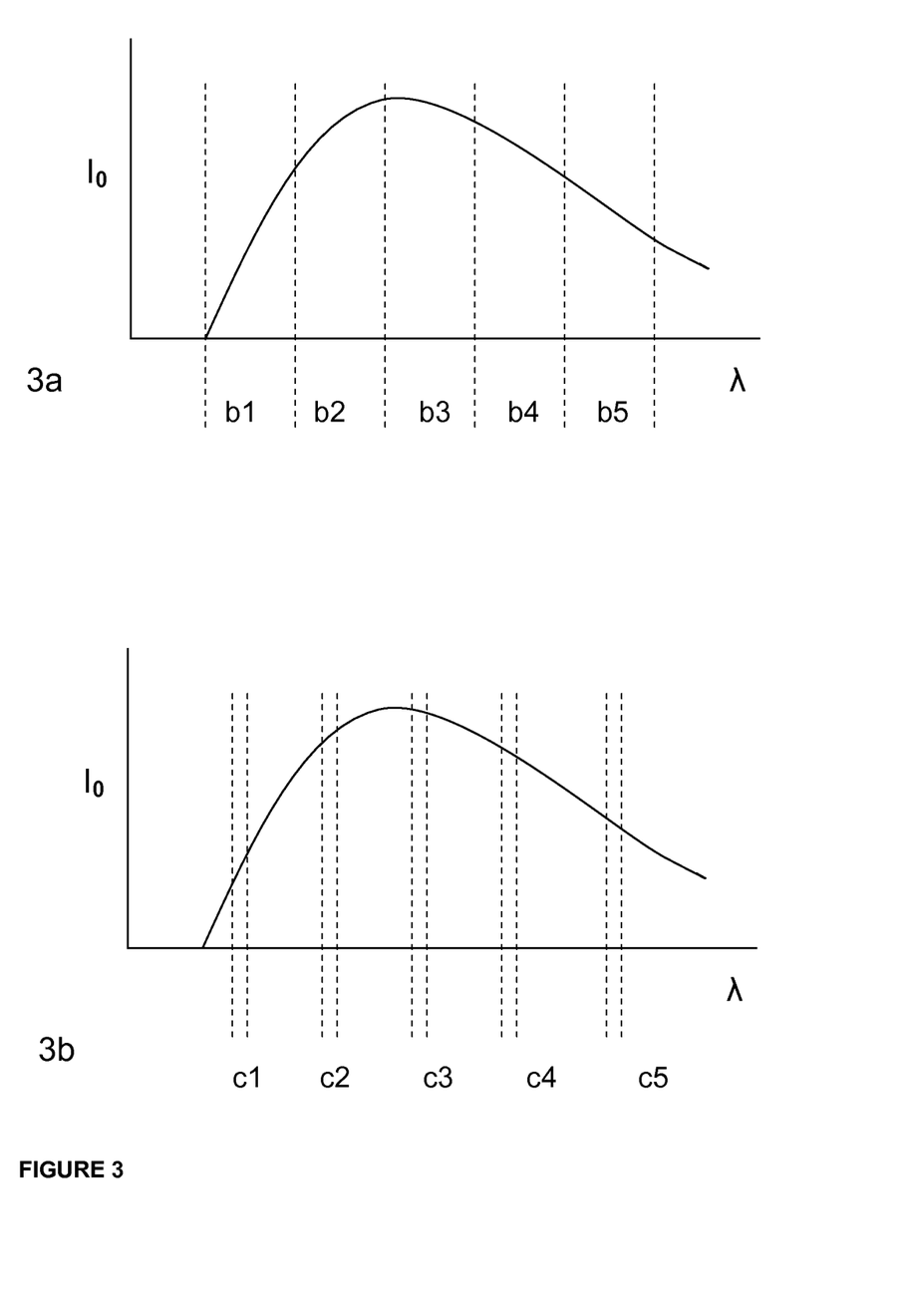
FIG. 3 illustrates a typical radiation source spectrum, and illustrates how it may be partitioned into plural energy bins to implement the invention.

The main purpose of FIG. 3 is to illustrate two possible ways in which the spectrum may be resolved in accordance with a possible embodiment. In each case, the spectrum is shown resolved across five frequency bands.

The schematic illustrates two ways in which the spectrum may be resolved. In FIG. 3a, the bulk of the generated spectrum is divided between five relatively broad energy bands b1 to b5. In FIG. 3b, five relatively narrow bands, which may approximate even to individual energies, are defined c1 to c5. Neither alternative is in contradiction with the principles of the invention, and any combination may be used to generate useful results for the numerical analysis employed by the invention. Additionally, although the calibration population process of the invention is primarily directed to apparatus which identify contents of an object by data analysis, the apparatus may also provide for an imaging function to assist in the identification of unknown objects. Such an imaging principle is well known. If an imaging function is used, the spectroscopic resolution may similarly be used to generate a spectroscopically resolved image. For example, one or other of the spectrum divisions illustrated in FIG. 3 could be used for spectroscopically resolved imaging to give further information about an object and contents under investigation.

In an example embodiment, the same principles may be used to generate general intensity data for a range of bottles and unknown contents, and to populate a database of intensity data for known bottles and contents, and thus to characterise and identify the material contents of an unknown bottle under investigation. In the example embodiment, the data is analysed numerically. The processor 32 further acts in relation to a series of identified frequency bands, for example those in FIG. 3a or 3b, and in this function uses the data to generate a representative quantification of, and for example an average of, transmitted intensity in each band, which is then passed to the intensity data item register 34 for storage.

In a first stage of populating a global reference database a library of data is generated of intensity information for contained liquids of known composition in known containers by scanning and determining attenuation of a range of known liquid/containers. The database provides reference information for a range of likely liquid/container combinations, thereby providing an accurate and rapid matching process for target liquids. In this way, a scanned container can be matched against the database of characteristics and a target liquid indentified. A method of populating such a library is described in more detail below.

An object under test comprising an unknown contained liquid may then be scanned in a second stage.

A comparator 36 compares the data thereby produced through the depth of the bottle with a library of data 37. The library of data includes pre-stored data of similar or at least numerically comparable nature which is related to or depends upon the expected attenuation of transmitted intensity, for example including the mass attenuation constant for a range of materials, and in particular specified target materials. The library of data includes intensity information for contained liquids of known composition in known containers across the spectrum of the radiation source for multiple permutations of different path lengths. This may be a manually or automatically addressed library. Data may be preloaded, or may be generated or added to over time by operation of the apparatus with known materials.

By virtue of this comparison, inferences may be drawn about the likely material content in the transmission path. This may be displayed on the display means 38 or the display can preferably be delayed until the scan cycle is completed as described below.

Figure 4:
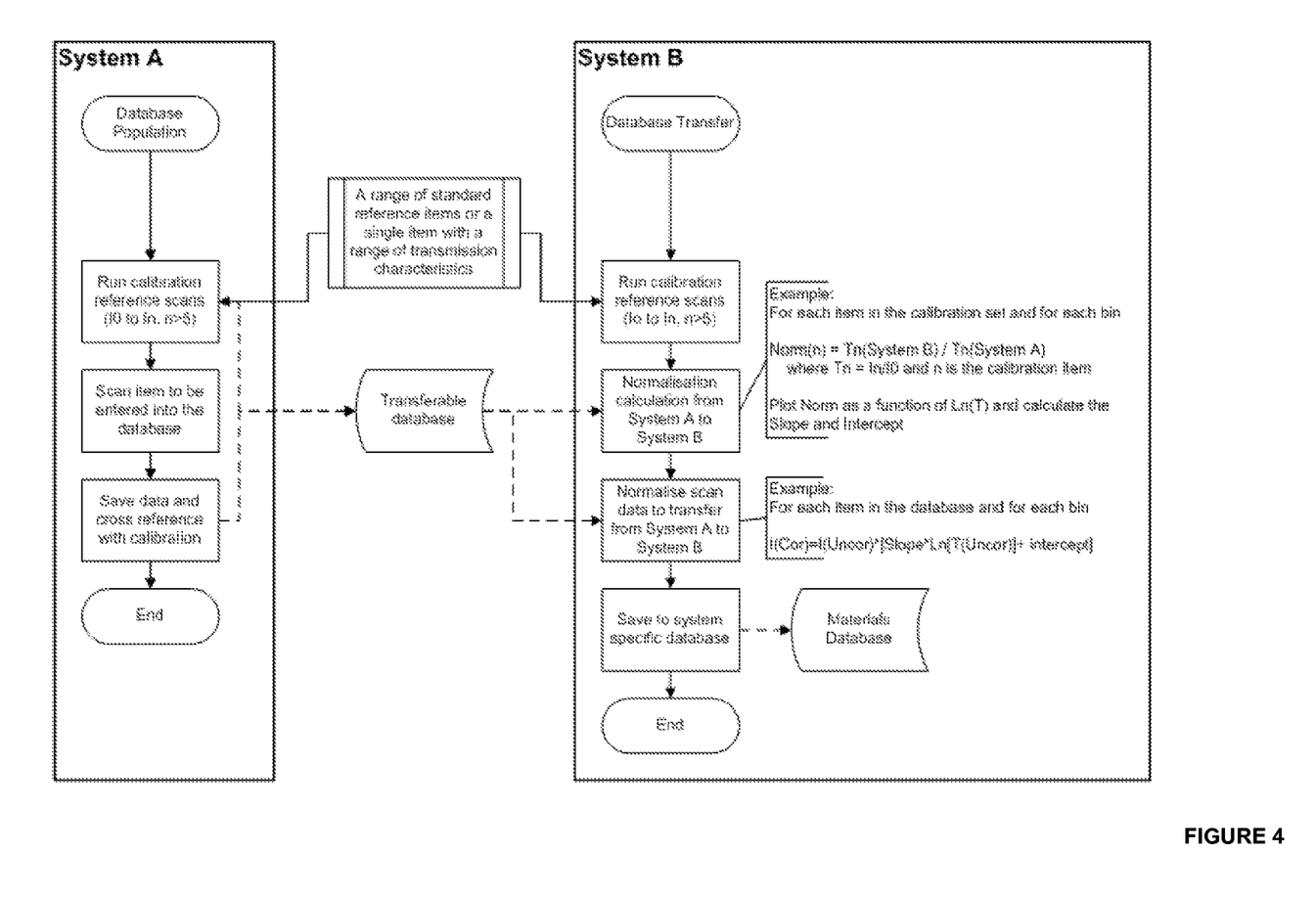
FIG. 4 illustrates a representative protocol for production of a dynamic database library of data calibrated for a system such as illustrated in FIG. 2 from data which has been collected and transferred from other such system(s)

FIG. 4 is a simple schematic illustration of a plausible protocol by which reference information generated on a first system (system A) in accordance with the above may be transferred to a second system (system B) in accordance with the above and dynamically adjusted in a manner which makes the reference data dynamically calibrated to the physical characteristics of the second system. Thus, the first and second stage referred to above may more readily be carried out on different systems without loss of data compatibility. The example protocol of FIG. 4 is an example protocol applicable to the example apparatus or any other apparatus to which a reference database embodying the principles of the invention could be applied, and is not limited to the example apparatus.

Considering the population of a transferable database by a plurality of machines or machine conditions M1, M2 etc (each constituting a "System A" on the flow chart), and the use of this database to populate a dynamic database on a machine to be calibrated (constituting a "System B" on the flow chart), the following general discussion can be made about the protocol to be followed.

Before a machine is populated for a first set of machine conditions M1 a calibration procedure is followed to generate a calibration dataset $CD_{M1}$. A calibration dataset comprises calibration data items for a plurality of scanning conditions at a plurality of energy bins. Preferably at least three and preferably at least five energy bins are used for each data item. Preferably, at least five data items are collected corresponding to scanning data for a range of standard object materials and/or thicknesses. In a convenient embodiment a standard object of single homogeneous material may be used comprising at least five such discrete thicknesses.

Figure 5:
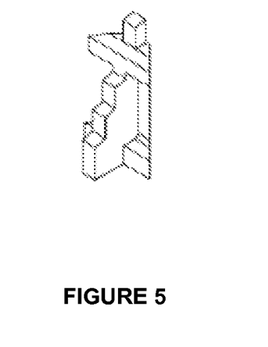
FIG. 5 illustrates a standard object for use in the protocol of FIG. 4.

An example standard object is shown in FIG. 5. This comprises a standard stepped block wedge block of nylon material. This provides a plurality of discrete thickness in a standard object which gives excellent reproducibility. Essentially identical standard objects can thus be provided to calibrate multiple systems to essentially identical standard.

A component database of transferable intensity-related information for a range of scan items is then generated, to comprise a population dataset $PD_{M1}$. For each component making up the population dataset a scan is performed of the relevant scan item, and emergent intensity data is resolved into plurality of energy bins. To allow the data for the scan item to be correlated with the calibration data, it is likely to be preferable that these energy bins are identical to those used in the calibration step.

This population dataset $PD_{M1}$ is tied in cross-referenced manner to $CD_{M1}$. The process may be repeated for second and subsequent machine conditions to generate further population datasets ($PD_{M2}$ etc) for further scan items tied to further calibration datasets ($CD_{M2}$ etc). Reference herein to different machine conditions may include populations generated on different machines, populations generated on the same machine at different times, for example under different operational parameters etc.

The multiple component databases $PD_{M1}$, $PD_{M2}$ which have been generated thereby can be merged into a global transferable database TD. Each data item in the global transferable database remains linked to the calibration dataset generated at the time it was produced. The global transferable database is thus transferable by means of the relative calibration procedure of the first aspect of the invention to any additional machine of the same general type subject to running off the same standard calibration protocol and to application of an appropriate transfer function to each data item. This represents the transfer to a System B in the flow chart.

To give effect to this, the transfer database TD is held on a suitable data register accessible by the System B machine to be calibrated/populated. The transfer database may be held locally, for example on the data register comprising a part of the System B machine or located locally thereto, or be held elsewhere in data communication with the machine, for example on a central database accessed via a distributed network.

In order to calibrate the System B machine for a given operational set of conditions Mx a calibration procedure is followed to generate a calibration dataset $CD_{Mx}$. All calibration datasets in accordance with the procedure are generated in numerically compatible manner, and for example using identical calibration standards such as the block wedge of FIG. 5. This makes it possible to generate a transfer function for each population dataset $PD_{M1}$, $PD_{M2}$ making up the global dataset TD by deriving a numerical relationship between the respective calibration datasets $CD_{M1}$, $CD_{M2}$ used in their generation and the calibration dataset $CD_{Mx}$ of the System B machine to be populated.

A suitable transfer function comprises a function which applies a correction factor to each data item in the transferable database so that it more accurately reflects an expected data item which would be generated on the System B machine to be populated under machine conditions Mx. In a convenient embodiment, the transfer function may comprise performing a simple normalisation step at each energy bin to apply a scaling factor to a data item from the transferable database to render it applicable to the dynamic database of the machine to be populated.

Thus, System B in the figure may be populated by a plurality of reference sources derived from Systems A in a dynamically matched and usable manner.

The invention claimed is:

1. A method of calibration of a dataset produced by an apparatus for scanning an object by causing incident radiation to impinge upon the object in a scanning zone and collecting spectroscopically resolved emergent intensity information of radiation after interaction with the object for use with a further apparatus for scanning an object, comprising the steps of:

generating an apparatus condition specific calibration dataset of emergent radiation intensity information generated after interaction in the scanning zone of at least one standard object spectroscopically resolved into a plurality of frequency bands;

populating a transferable database comprising a dataset of transferable data items of emergent intensity information for a range of possible component materials, each data item comprising emergent radiation intensity information for the material spectroscopically resolved into a plurality of frequency bands, and each data item being linked to a calibration dataset of emergent radiation intensity information generated by the said at least one standard object specific to the apparatus condition used to generate the said data item spectroscopically resolved into a plurality of frequency bands;

generating an apparatus condition specific calibration dataset for the further apparatus to be used comprising emergent radiation intensity information generated after interaction in the scanning zone of at least one standard object spectroscopically resolved into a plurality of frequency bands for an apparatus condition of the apparatus to be used;

for each transferable data item:

generating a transfer function from the functional relationship between the calibration dataset linked to the data item and the calibration dataset generated for the apparatus to be used by numerical comparison of the calibration dataset for the apparatus to be used and the calibration dataset for the apparatus used to generate each data item; and applying the transfer function to the transferable data item to generate a dynamic data item adjusted to the apparatus to be used;

thereby populating a data register addressable by the apparatus with a dynamic dataset comprising a dataset of data items of emergent intensity information for a range of possible component materials each dynamically adjusted to the apparatus to be used.

2. A method in accordance with claim 1 wherein, during the calibration step, reference data is generated for a plurality of frequency bands in relation to at least two standard reference points so that a calibration can be fitted between them by generation of a suitable transfer function.

3. A method in accordance with claim 2 wherein a calibration step provides for calibration measurement at a plurality of material thickness or for a plurality of material compositions.

4. A method in accordance with claim 3 wherein plural standard objects are provided of different known thickness or composition.

5. A method in accordance with claim 3 wherein a standard object is provided that defines plural standard reference points defining plural portions of different known thickness or composition.

6. A method in accordance with claim 1 wherein the calibration step is additionally modified to correct further for apparatus response over a range of varied conditions.

7. A method in accordance with claim 1 applied to objects comprising containers of contained materials which by their nature will be expected to have a single generally homogeneous composition, comprising fluid compositions including liquids, including mixtures, solutions, emulsions, and suspensions, like flowable compositions including gels, pastes, creams, and fine powders, and aerosols.

8. A method in accordance with claim 1 wherein the transferable database is built up by generation of population data items during one or more processes comprising: specific operation of a machine for that purpose and operation of the machine for its primary intended purpose.

9. A method in accordance with claim 1 wherein the method comprises the further steps of:

generating a material specific transferable data item comprising emergent radiation intensity information generated after interaction in to the scanner zone of an object of known material composition and/or identity spectroscopically resolved into a plurality of frequency bands;

linking the material specific transferable data item to the apparatus specific calibration dataset generated previously;

passing the foregoing information to the transferable database to further populate the transferable database.

10. A method in accordance with claim 1 wherein one or more standard objects are used providing for calibration measurement at a plurality of material thickness or for a plurality of material compositions.

11. A method in accordance with claim 10 wherein a standard object is used comprising a standard block of known material with a plurality of discrete thickness.

12. A method in accordance with claim 1 wherein a first standard object is used to calibrate a first system which generates data for a transferable database and an essentially identical second standard object is used to obtain a calibration dataset on the system to be calibrated and populated with a dynamic database.

13. A method in accordance with claim 1 wherein radiation is resolved spectroscopically across and differentiated simultaneously into at least five energy bands within the source spectrum.

14. A method in accordance with claim 1 wherein radiation is resolved spectroscopically across and differentiated simultaneously into a plurality of energy bands within the source spectrum by use of a detector exhibits a spectroscopically variable response across at least a substantial part of the spectrum of the radiation source allowing detailed spectroscopic information to be retrieved.

15. A method in accordance with claim 14 wherein the detector is selected from cadmium telluride, cadmium zinc telluride (CZT), cadmium manganese telluride (CMT) and alloys thereof.

16. A method in accordance with claim 15 wherein the detector comprises crystalline $Cd_{1-(a+b)}Mn_aZn_b Te$ where $a+b<1$ and a and/or b may be zero.

17. A method of identifying the composition or identity of an object which comprises calibrating a scanner apparatus and populating a scanner apparatus with a dynamic dataset in accordance with claim 1, causing an object of unknown composition or identity to be placed into a scanner zone between a radiation source and a radiation detector system spaced therefrom;

obtaining a dataset of emergent radiation produced by the object in the scanner zone after interaction with incident radiation;

resolving the collected emergent intensity data spectroscopically across a plurality of frequency bands in the spectrum of the source;

comparing the resolved intensity data with intensity data items in the dynamic dataset;

obtaining thereby an indication of the material content or identity of the object.

18. A method of identifying an object according to claim 17, wherein the intensity data items in the populated dynamic dataset comprises a library of spectra for known objects, wherein the comparing comprises comparing the spectroscopically resolved intensity data for the unknown object with the spectra in the library, and the obtaining comprises indicating which of the spectra in the library matches the data for the unknown object or indicating that none of the spectra in the library matches.

19. A method of generation of a transferable reference database for an apparatus for scanning an object by causing incident radiation to impinge upon the object in a scanning zone and collecting spectroscopically resolved emergent intensity information of radiation after interaction with the object, and of populating a specific apparatus with a dynamic reference database derived therefrom, comprises the steps of:

generating an apparatus specific calibration dataset of emergent radiation intensity information generated after interaction in the scanning zone of at least one standard object spectroscopically resolved into a plurality of frequency bands;

generating a material specific transferable data item comprising emergent radiation intensity information generated after interaction in the scanning zone of an object of known material composition and/or identity spectroscopically resolved into a plurality of frequency bands;

linking the material specific transferable data item to the apparatus specific calibration dataset;

repeating the preceding two steps for a plurality of objects of known material composition or identity to populate a transferable database comprising a dataset of transferable data items of emergent intensity information for a range of possible component materials; and applying the transferable database to the method of any preceding claim.

* * * * *